(12) United States Patent
Arts et al.

(10) Patent No.: US 11,221,282 B2
(45) Date of Patent: Jan. 11, 2022

(54) MEASUREMENT ARRANGEMENT AND MEASUREMENT METHOD FOR DETERMINING A CONSTITUENT SUBSTANCE OR QUALITY PARAMETER OF WATER OR WASTE WATER

(71) Applicant: LAR Process Analysers AG, Berlin (DE)

(72) Inventors: Werner Arts, Berlin (DE); Wolfgang Genthe, Berlin (DE)

(73) Assignee: Lar Process Analysers AG

( * ) Notice: Subject to any disclaimer, the term of this patent is extended or adjusted under 35 U.S.C. 154(b) by 429 days.

(21) Appl. No.: 16/299,741

(22) Filed: Mar. 12, 2019

(65) Prior Publication Data
US 2019/0277818 A1    Sep. 12, 2019

(30) Foreign Application Priority Data
Mar. 12, 2018   (DE) .......................... 102018105611.7

(51) Int. Cl.
*G01N 33/18*        (2006.01)
*G01N 31/12*        (2006.01)
(Continued)

(52) U.S. Cl.
CPC ................. *G01N 1/44* (2013.01); *G01K 1/14* (2013.01); *G01N 1/14* (2013.01); *G01N 31/12* (2013.01);
(Continued)

(58) Field of Classification Search
CPC .. G01K 1/14; G01N 1/14; G01N 1/44; G01N 2001/1463; G01N 31/12; G01N 33/18;
(Continued)

(56) References Cited

U.S. PATENT DOCUMENTS 6,143,568 A * 11/2000 Pilz .................... G01N 31/12
                                                 436/114
6,447,725 B1 * 9/2002 Inoue ................. G01N 33/1846
                                                 422/78

(Continued)

*Primary Examiner* — Maureen Wallenhorst
(74) *Attorney, Agent, or Firm* — Donald R. Boys; Central Coast Patent Agency LLC

(57) ABSTRACT

Measurement arrangement for determining a constituent substance or quality parameter of water by thermal decomposition in a reaction module, delivery of a reaction product to a detector, and evaluation of a detector signal for deriving a value of the constituent substance or quality parameter, wherein the reaction module is an elongated vessel having internal heating, and has a head section into which the sample is introduced, a reaction zone, as well as a foot section, from which the reaction product is output, wherein the reaction module, the heating, and means for the supply of samples and carrier gas are configured such that during the operation of the measurement arrangement an outer head temperature is $T_H \leq 80°$ C., and an outer foot temperature is $T_F \leq 150°$ C. at a maximum temperature in the reaction zone of $T_{MAX} \geq 1150°$ C.

14 Claims, 3 Drawing Sheets

Figure 1:
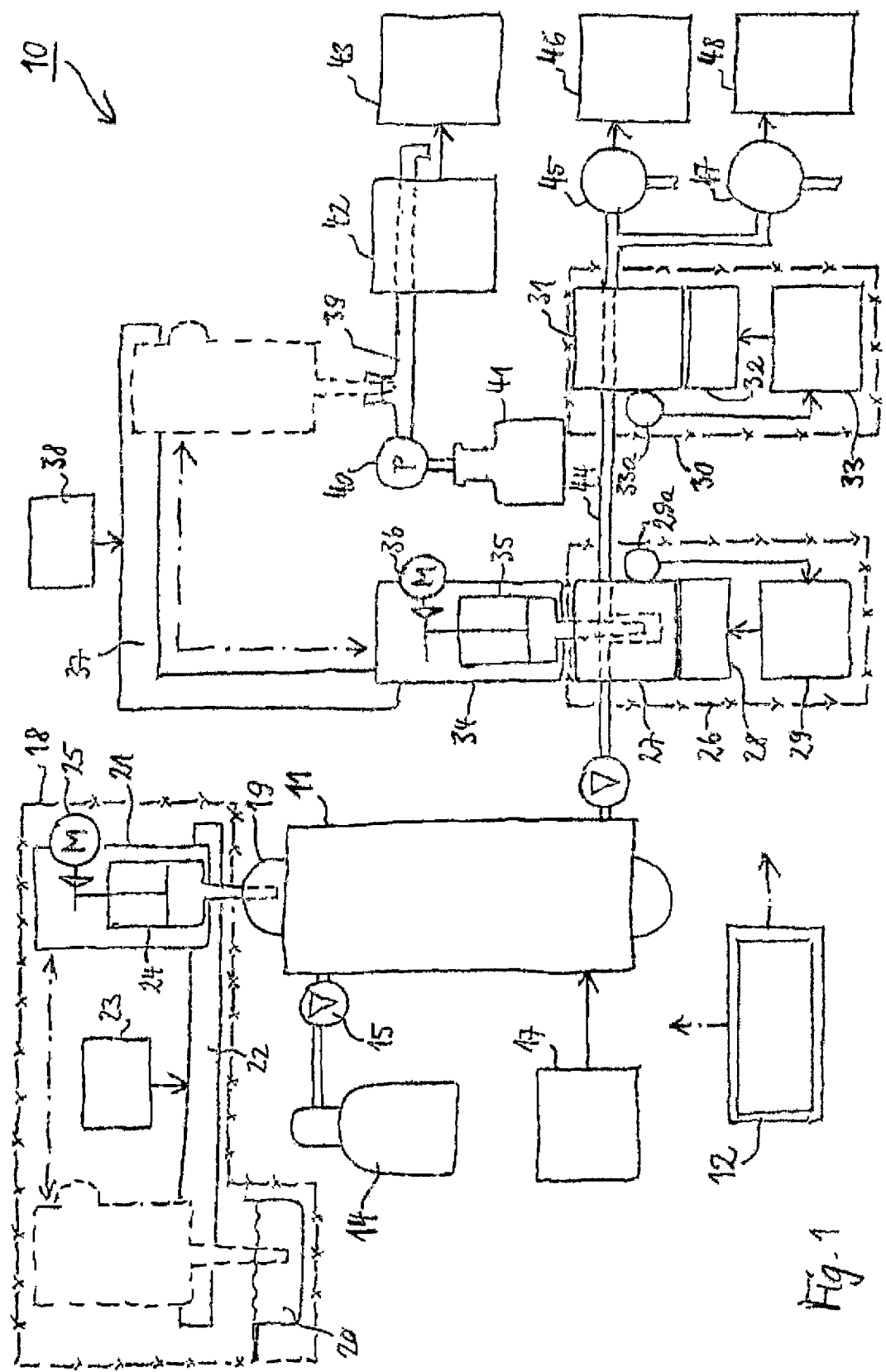

(51) Int. Cl.
    *G01N 1/44*     (2006.01)
    *G01K 1/14*     (2021.01)
    *G01N 1/14*     (2006.01)
(52) U.S. Cl.
    CPC ..... *G01N 33/1806* (2013.01); *G01N 33/1846* (2013.01); *G01N 2001/1463* (2013.01)
(58) Field of Classification Search
    CPC .......... G01N 33/1806; G01N 33/1826; G01N 33/1846; Y10T 436/16; Y10T 436/17; Y10T 436/177692; Y10T 436/178459; Y10T 436/179228; Y10T 436/20; Y10T 436/204998; Y10T 436/207497; Y10T 436/23; Y10T 436/235; Y10T 436/25875
    USPC ........ 436/103, 106, 116, 117, 118, 127, 133, 436/136, 145, 146, 149, 150, 152, 155, 436/157, 160, 181; 422/78, 79, 80, 94
    See application file for complete search history.

(56)               References Cited

U.S. PATENT DOCUMENTS

| | | | |
|---|---|---|---|
| 6,458,328 B1* | 10/2002 | Wreyford | G01N 31/12 |
| | | | 422/69 |
| 7,803,631 B2* | 9/2010 | Arts | G01N 33/1846 |
| | | | 436/146 |
| 7,993,930 B2* | 8/2011 | Genthe | G01N 33/182 |
| | | | 436/103 |
| 10,073,073 B2* | 9/2018 | Bettmann | G01N 33/1846 |
| 2006/0019403 A1* | 1/2006 | Arts | G01N 33/1806 |
| | | | 436/160 |
| 2019/0302085 A1* | 10/2019 | Yano | G01N 31/12 |

\* cited by examiner

MEASUREMENT ARRANGEMENT AND MEASUREMENT METHOD FOR DETERMINING A CONSTITUENT SUBSTANCE OR QUALITY PARAMETER OF WATER OR WASTE WATER

The invention relates to a measurement arrangement and/or a measurement method for determining a constituent substance or quality parameter of water or waste water.

For determining the content of certain constituent substances of water—and thus the quality of drinking water, process water or else sea water, and of waste water contaminated by organic substances, nitrogen compounds or similar—it is known to evaporate and burn a sample in an atmosphere of inert transport gas (carrier gas) enriched with oxygen and to supply the combustion gas mixture obtained on this occasion to a detector adapted for the detection of carbon dioxides, nitrogen dioxides, etc.

As the detectors, (apart from others) infrared detectors have proven their value for the carbon content, special chemiluminescence detectors, respectively electrochemical sensors have proven their value for the nitrogen content, and so-called coulometric detectors have proven their value for the halide content.

Detection methods based on the combustion of a water sample for capturing the content of organic constituent substances—the so-called TOC (total organic carbon)—have gained great dissemination. Here, a small amount of water together with the transport gas is supplied to a furnace heated to a predetermined temperature by means of resistance heating, where it is evaporated and burnt almost immediately, and the combustion gas is supplied to a NDIR $CO_2$ detector whose display of the $CO_2$ content constitutes a measure for the C content of the water sample. An advanced realization of this method and a corresponding apparatus are described in DE 43 44 441 C2. An arrangement modified to measure very low TOC values—such as in ultra-pure water or ultra-pure solutions for medical applications—is described in EP 0 684 471 A2.

In the documents EP 0 887 643 B1 and EP 1 055 927 B1, the Applicant proposed further developed methods of this kind and appropriately designed reactors or general arrangements. An improved loading of samples in such a measurement arrangement is the subject matter of the Applicant's document WO 2016/091252 A2.

Document U.S. Pat. No. 5,702,954 describes a multi-stage decomposition method for phosphorus-containing vegetable or animal samples of the phosphate content including combustion in the presence of a reducing agent (such as oxygen) and subsequent conversion along with ozone in a further reaction chamber at ambient temperature. Document US 2003/0032194 A1, as well, describes a multi-stage oxidation method which had been developed primarily for determining nitrogen and sulfur but also phosphorus in a sample containing one of these elements. Thermal decomposition methods using special catalysts or ozone, for example, are also known from JP 59154358 A or JP 61140863 A.

A measurement arrangement and a measurement method for determining the phosphorus content of waste water samples, which is based on the Applicant's patents/applications mentioned above, are described in the Applicant's document EP 2 115 453 B1.

The invention is based on the task to propose an improved measurement arrangement and an improved measurement method, which can be employed for various constituent substances of water or quality parameters, allow for a cost-efficient decomposition of the samples and are easy and safe to handle in practice.

This task is solved in its device aspect by an arrangement having the features of claim 1, and in its method aspect by a method having the features of claim 8. Appropriate further developments of the inventive idea are the subject matter of the depending claims.

The invention includes the idea of reducing the heat losses on the reaction module of the measurement arrangement by suitable constructional and control measures, and in particular of limiting housing temperatures of the reaction module in its head and foot area which are critical during operating procedures. The maximum temperature required in the reaction zone for efficient sample decomposition should be guaranteed at the same time. The proposed reaction module and its operation method is specifically characterized in that the reaction module, the resistance heating or infrared heating, and means for the supply of samples and carrier gas are configured such that during the operation of the measurement arrangement an outer head temperature is $T_H \leq 80°$ C., and an outer foot temperature is $T_F \leq 150°$ C. at a maximum temperature in the reaction zone of $T_{MAX} \geq 1150°$ C.

These measures allow a considerable reduction of the energy consumption of the reaction module and thus of the measurement arrangement as a whole to be achieved, on the one hand, which represents a considerable advantage of practical use for the users in case of a mobile operation with accumulators or batteries. On the other hand, this makes the handling of the measurement arrangement even safer and easier, and this, as well, represents a considerable advantage for the user.

In a realization of the invention, the reaction module, the resistance heating or infrared heating, and means for the supply of samples and carrier gas are configured such that during the operation of the measurement arrangement a head temperature is $T_H \leq 150°$ C., and a foot temperature is $T_F \leq 150°$ C., in particular 120° C., wherein the maximum temperature in the reaction zone is $T_{MAX} \geq 1200°$ C. in particular.

The proposed reaction module and operation method may be used in a modular manner in various measurement arrangements which are designed inter alia for determining nitrogen and/or phosphorus and/or the content of organic carbon, TOC, or the chemical oxygen demand, CSB.

In advantageous constructional realizations of the invention, it is provided for the reaction module to have a two-layer or multi-layer thermal insulation comprising a macroporous layer and a microporous layer. In this case, in particular one of the layers of the thermal insulation is formed by prefabricated annular resistance heating/ceramic fiber modules, which are known and commercially available under the trade name Fibrothal®, for example.

In a further appropriate realization, the reaction module is mainly filled with a filling of porous ceramic balls. The selection of suitable ceramic balls having a size and porosity matched to the case of application, allows the passage or the dwelling time of the sample in the reaction zone, and possibly specifically also the dwelling time of the sample in various temperature ranges of the reaction zone and thus the T regime of the reaction module as a whole to be optimized. In practice-oriented realizations, Al2O3 balls are used, which specifically have mean diameters of 6, 4.5, 2.7 and 1.2 mm, wherein at least two, preferably four layers of balls each having different diameters lie on top of each other, and the thickness of the individual layers may be selected such with respect to the specific application and method conditions that the oxidation of the constituent substances of water relative to the analytes in the measurement gas is reliably guaranteed in the different temperature zones of the reactor.

In practice, realizations have proven to be appropriate, in which the reaction module has an inner wall (or a separate reaction vessel) of Al2O3 extending at least along the length of the reaction zone, and in the head and foot areas in each case an CFC insert having an O-ring with a Teflon sheathing as a sealing element.

Aluminum oxide as the reactor material has sufficient temperature resistance and heat conductivity for the operating conditions, and furthermore sufficient temperature change resistance for practical operation. In case of a potential reduction of the decomposition temperature, high-performance stainless steel may also be used. The furnace head in particular is made of a mechanically reinforced fluorinated hydrocarbon for thermal insulation. According to the application, the furnace foot either is made of a mechanically reinforced fluorinated hydrocarbon or of a glass foot having a ceramic baffle plate for thermally bypassing the hot reaction gas.

In practice-oriented realizations, the head section of the reaction module has an injection port for temporarily introducing an injection needle or permanently supporting a small supply tube, which injection port comprises an O-ring which is internally spring-loaded by a silicon padding or an inserted spring.

In adaptation to this realization, the measurement arrangement specifically comprises an injection syringe operated by a compression spring or a step motor for inputting the sample into the reaction module. This kind of loading of the reaction module with a sample is known as such in particular from prior property rights/applications of the Applicant. As to details of this loading method, reference may therefore be made to the prior art such as the document WO 2016/091252 A2. Here, a detector is in particular assigned to the compression spring or the step motor for detecting the start of an injection process of the sample into the reaction module. This idea of detecting the injection process in conjunction with the use of the detection signal described further below is novel.

An alternative realization of the reaction module has a three-way valve connected to the small supply tube for optionally introducing the sample or a rinsing liquid into the reaction module. Here, as well, preferably a detector is assigned to the element causing the sample to be supplied, that is to say the three-way-valve, for detecting the start of the injection process of the sample into the reaction module. According to the inventors' studies, this realization has advantages with respect to the wear resistance of the seal(s) and thus of the maintenance expenditure for the measurement arrangement, but may also be advantageous with respect to the speed of the sample supply and the rapid alternating execution of measurement and rinsing processes.

In further realization, setting means are provided at the injection port for setting the position of the injection needle or the small supply tube in the reaction module. Such settings allow the temperature progress in the reaction module and in particular also the temperatures at its head and foot areas to be influenced to a certain extent.

A realization serves likewise the purpose of a targeted setting of the temperature progress in which the resistance heating or infrared heating comprises a plurality of vertically arrayed, separately driven heating elements, in particular separate resistance heating/ceramic insulating modules. Here, in particular, a temperature sensor and a corresponding control input of a heating control device is assigned to at least one of the heating elements, and the heating control device is configured such that a heating current can be applied, in particular individually, to the heating modules as a function of an output signal of the temperature sensor and in accordance with a predetermined temperature profile of the reaction module.

In a further realization, a heating control device of the resistance heating or infrared heating has a detector input for receiving an injection input signal representing a proceeding introduction process of a sample, and the heating control device is configured such as to vary the heating power of the resistance heating or infrared heating based on the injection input signal. This measure may in particular be advantageously combined with the above-mentioned temperature sensor control of the resistance heating or infrared heating, in order to thus take into account the influence of the sample injection process on the temperature distribution within the reaction module in a differentiated manner.

According to the inventors' investigations, a PID control algorithm is advantageously implemented in the heating control device, which algorithm utilizes at least the output signal of a temperature sensor and, optionally, the injection input signal for the temperature regulation in the reaction module.

On the other hand, the control of the measurement arrangement may be configured such that the means for sample supply and carrier gas supply have a supply control device for the automatically controlled sample supply and carrier gas supply which has in particular at least one input terminal for receiving an input signal delivered from the heating control device for influencing the automated sample supply and carrier gas supply. Here, the sample injection is thus controlled to some extent considering the current temperature conditions in the reaction module, and is varied, if need be, with respect to a standard regime.

Method aspects of the invention will largely result from the device aspects explained above and will therefore not be described again in more detail here.

However, reference is made to the aspect that during the input process of a sample into the reaction module, an injection input signal is generated for a heating control device of the resistance heating or infrared heating, and the heating control device is operated such as to vary the heating power of the resistance heating or infrared heating based on the injection input signal.

Furthermore, reference is made to the aspect that at least one temperature sensor is assigned to heating elements of the resistance heating or infrared heating, and the signals of the or of each temperature sensor are supplied to corresponding control inputs of the heating control device, and the heating control device is operated such as to apply a heating current to the heating elements as a function of an output signal of the associated temperature sensor and in accordance with a predetermined temperature profile of the reaction module.

Reference is moreover made to the fact that a PID control algorithm is advantageously operated in the heating control device such as to utilize at least the output signal of a temperature sensor and, optionally, the injection input signal for the temperature regulation in the reaction module. Ultimately, it may be provided for the means for sample supply and carrier gas supply to have a supply control device for automatically controlled sample supply and carrier gas supply and to be operated such that temperature fluctuations within the reaction zone are minimized.

Figure 2:
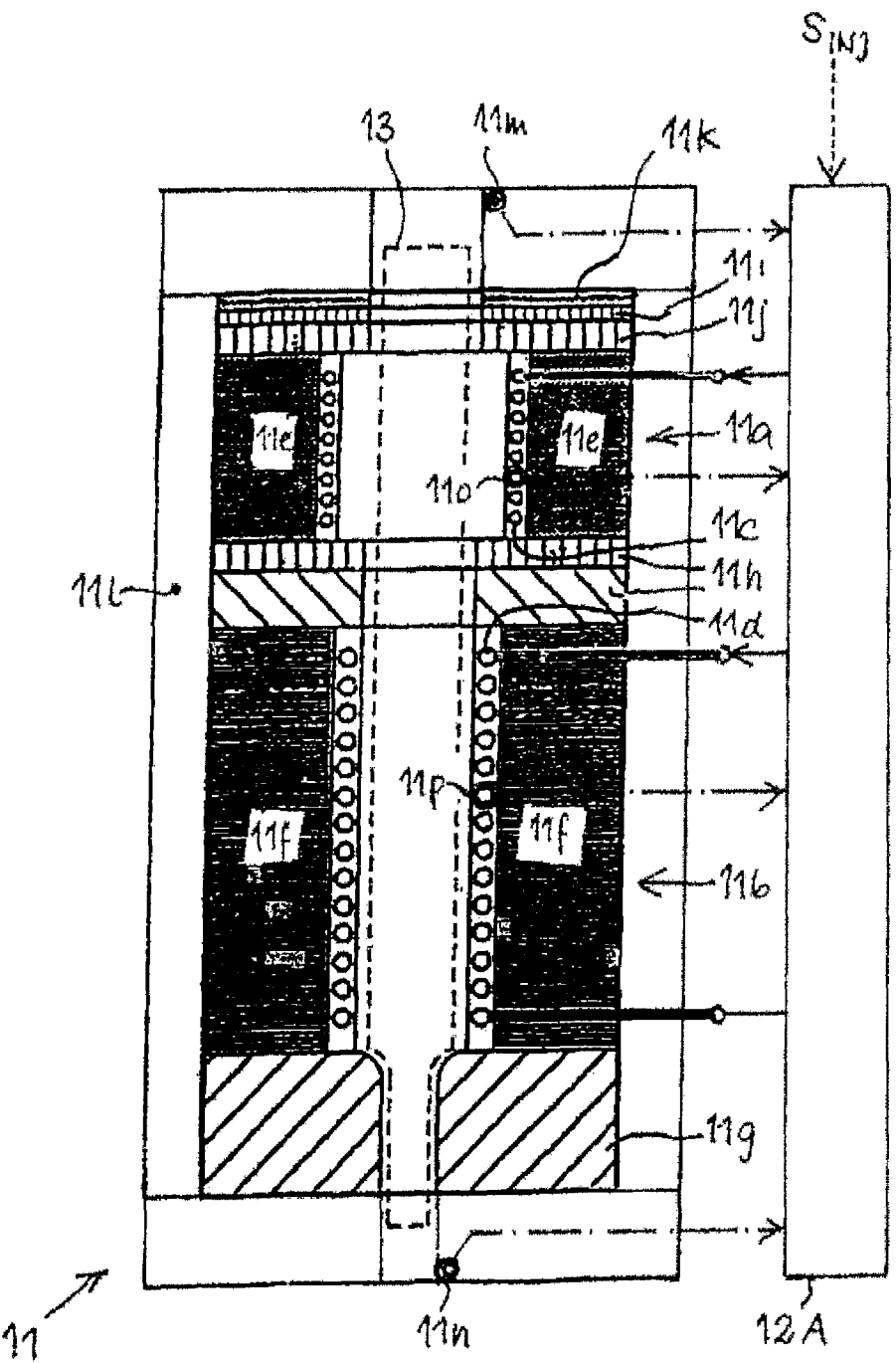
Figure 3:
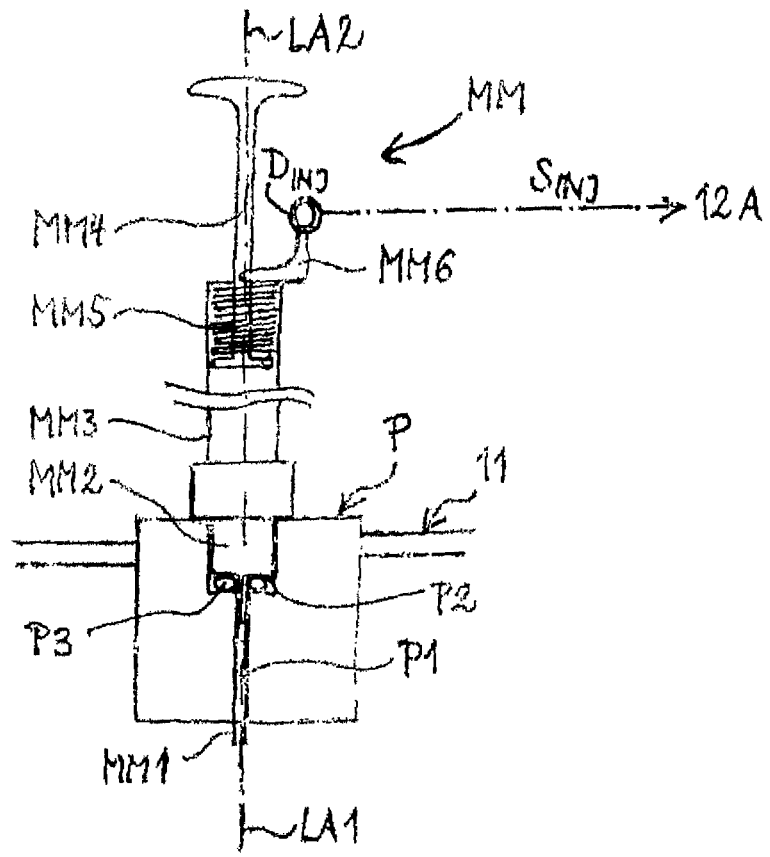
Figure 4:
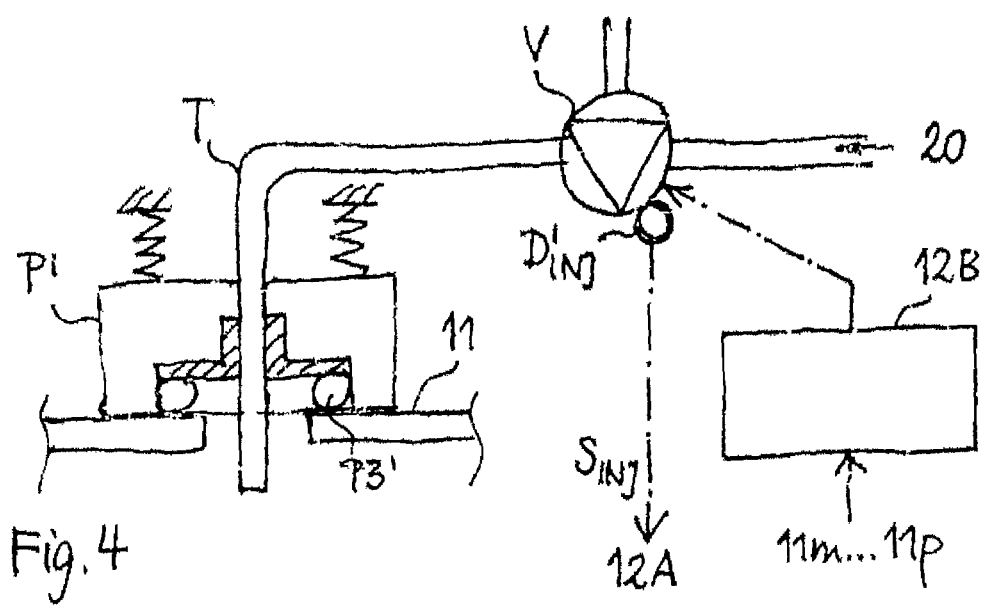

Advantages and expedient features of the invention incidentally will result from the following description of an exemplary embodiment and substantial realization aspects of the invention on the basis of the Figures. Shown are in:

FIG. 1 a diagrammatic overall representation of an arrangement according to the invention, FIG. 2 a schematic cross-sectional representation of the substantial portions of a reaction module of a measurement arrangement according to an embodiment of the invention, FIG. 3 a schematic longitudinal cut representation of an injection syringe with an injection needle introduced into the injection port according to an exemplary embodiment of the analysis arrangement, and FIG. 4 a schematic diagram of a further realization of the loading of a sample into a measurement arrangement according to the invention.

In the manner of a schematic diagram, FIG. 1 shows the overall structure of an exemplary measurement arrangement 10 for determining various constituent substances of waste water or service water. The main component of the arrangement 10 is a reaction module 11 described further below; but another type of combustion furnace (such as with a radiation heating) may as well be employed instead. For the sake of clarity of the representation, parts which are not essential to the invention and, for instance, serve the purpose of calibrating and cleaning the measurement arrangement, are omitted in this schematic representation.

A symbolically depicted control unit (controller) 12 controls the overall process of the sample decomposition and the measurement procedures and is of course connected to the essential shut-off, transport, heating and determination devices of the arrangement. The implementation, connection and operation of such a control device are within the skilled person's scope and are based on the method description given further below and the device structure explained hereinafter.

At the input side, a carrier gas storage 14 having an associated input valve device 15 is assigned to the reaction module 11 for providing the carrier gas for the measurement procedures. Furthermore, the furnace has a heating control unit 17 for controlling the electrical furnace heating, and a sample supply device 18 for supplying a sample into a sample injection valve 19 of the furnace.

The sample supply device 18 comprises a sample reservoir 20, which may be disposed at the inlet of a sewage plant, for example, an injection unit 21 mounted to be displaceable on a transport guide 22, and a corresponding transport control 23. The syringe unit 21 comprises a dosing syringe 24 and a step motor 25 for the precisely controllable actuation thereof and thus dosing of a predetermined sample volume.

At the outlet of the reaction module 11, a first cooling stage 26 is arranged comprising a cold trap unit 27, a Peltier cooler 28 and an associated temperature control 29 having a temperature sensor 29a on or in the cold trap unit 27. Downstream of the first cooling stage 26, a second cooling stage 30 is arranged comprising a cooling block 31 having an associated Peltier cooler 32 and a temperature control unit 33 controlling the Peltier cooler 32 and having a temperature sensor 33a.

A second syringe unit 34 is assigned to the first cooling stage 26, which second syringe unit 34—in analogy to the syringe unit 21 for loading the combustion furnace 1—has an injection syringe 35 with a step motor 36 for the precisely controlled actuation thereof. Moreover, this syringe unit 34 as well is supported on a transport guide 37 to which a transport control unit 38 is assigned for displacing the syringe unit into a second operational position. This operational position is above a flow-through cuvette 39 into which the needle of the injection syringe 35 may engage just as into the cold trap 27. In the Figure, this second operational position, just as the initial operational position of the syringe unit 21, are represented in dashed lines.

At an inlet of the flow-through cuvette 39, a reactant container 41 is connected via a pump 40, in which reactant container a chemical required for the photometrical determination of phosphorous is stored. The flow-through cuvette 39 protrudes into a photometer unit 42 configured for the photometric analysis of an aqueous sample flowing through the flow-through cuvette 39, and the outlet of which is connected to a phosphorous evaluation stage 43.

At the outlet of the second cooling stage 30, the output line 44 of the combustion furnace 1 branches out to an NO detector 45, which is connected to a nitrogen (TN) evaluation stage 46 at the outlet side, and to a $CO_2$ detector 47, which is connected to a carbon (TOC) evaluation stage 48 at the outlet side.

The operating mode of the measurement arrangement 13 partly arises from the above explanations regarding the inventive method but will briefly be summarized again hereinafter.

By means of the first syringe unit 21, an aqueous sample is taken from the reservoir 20, transported to the combustion furnace 1 and injected therein. At the temperatures set there, it will be evaporated and burnt immediately, and the resulting combustion gas is conducted out from the furnace into the output line 44 by means of a carrier gas flow fed from the carrier gas reservoir 14. In the condenser the flow of combustion gas/carrier gas is cooled down to a first cooling temperature, at which a condensate precipitates in the cold trap 27.

By means of the second syringe unit 34, a predetermined amount is withdrawn from this condensate and brought into the flow-through cuvette 39, where it is mixed with the reactant conveyed via the pump 40 for effecting a photometrical determination process and is supplied to the photometer unit 42 for phosphorous detection.

In the second cooling stage 30, the flow of combustion gas/carrier gas is cooled down to a second cooling temperature close to 0° C. and supplied to the gas detectors 45 and 46 for NO and $CO_2$ determination at the outlet side of the cooling stage. As a result of the determination processes at the detectors 42, 45 and 47, the corresponding evaluation stages 43, 46 and 48 determine the total phosphorous content (TP), the total nitrogen content (TN), and the total content of organic carbon (TOC) of the aqueous sample, which had been taken from the reservoir 20 and separated in the combustion furnace 1.

In a schematic cross-sectional representation, FIG. 2 shows essential sections of a sample combustion furnace (reaction module) 11 in a realization according to the invention, into which a substantially elongated cylindrical reaction vessel 13 of stainless steel (drawn in the Figure outlined in a dashed line) may be inserted. At the lower end (foot end), this reaction vessel 13 has a tubular outlet which can be cleaned easily from below for removing salt deposits.

In the shown special two-zone configuration (which is only explained here as an example), the furnace 11 has a first, upper heating zone 11a, where a maximum temperature of 800° C. can be reached in this realization, and a second, lower heating zone 11b, where a maximum temperature of 1250° C. is reached. Both of the heating zones are heated via heating modules 11c, 11d of a highly temperature resistant special alloy such as the material Kanthal-Fibrothal®, which modules are arranged in a hollow cylindrical manner around the corresponding portion of the reaction vessel 13.

Due to the different maximum temperatures, the heating modules 11c, 11d have microporous ceramic fiber insulations 11e or 11f of different thicknesses, and the foot area 119, the area 11 between the heating zones, and the head area 11i, 11j below an aluminum cover 11k are also ceramic fiber-insulated. A sample loading and carrier gas supply device (not illustrated in the Figure) is provided in the area above the cover 11k. The entire reaction module 11 moreover is coated with a microporous outer insulation 11l which considerably reduces both the temperature at the outer circumference of the furnace and on the head and foot thereof, and namely during normal operation of the furnace to the values mentioned further above.

The combustion furnace 11 has a complex temperature sensor system which is likewise able to contribute to reaching this goal. This temperature sensor system comprises a temperature sensor 11m, 11n in each case arranged in the head and foot area, as well as a temperature sensor 11o, 11p in each case assigned to one of the heating modules 11c, 11d. All of the temperature sensors are connected to corresponding inputs of a heating control and regulation device which, according to the designation of the controller 12 in FIG. 1, is designated 12A. In the heating control and regulation device 12A, the detection signals of the temperature sensors are processed into driving signals for the heating modules 11c, 11d according to a stored optimizing algorithm (if required, along with signals $S_{INJ}$, which characterize a sample injection process (see further below). The driving signals control the current supply to the modules and thus the heating of the heating zones 11a, 11b in a time-dependent manner. Advantageously, a PID control algorithm is implemented in the heating control and regulation device 12A.

The furnace structure shown in FIG. 2 and described above, together with the selective and controlled heating described, contributes advantageously to the permanent realization of the high temperatures of more than 1200° C. generated specifically in the second, lower heating zone 11c, with the special insulation both contributing to a reasonable energy expenditure and excluding hazards to the environment.

In a schematic manner, FIG. 3 shows an exemplary structure in a longitudinal cut representation and the mutually matched geometric configuration of the injection syringe MM and the injection port P of the furnace 11 (FIG. 2) of the measurement arrangement (FIG. 1).

The injection port P comprises a guiding sleeve P1 of a substantially cylindrical configuration in its longitudinal extension, whose diameter and length are matched to the corresponding dimensions of an injection needle MM1 of the injection syringe MM, and whose longitudinal axis coincides with a longitudinal axis LA1 of the furnace which is of a cylindrical configuration in its basic shape. At the upper side of the injection port P, a bore P2 having an enlarged diameter is provided, whose dimensions are matched to those of a needle collar MM2 of the injection syringe, and whose lower front surface acts as a stop for depth delimitation when the injection syringe is introduced. An O-ring P3, which may in particular be realized as a silicon ring with a Teflon coating, rests upon the lower front surface of the bore P2 as a seal. By means of this stop, an exactly predetermined position of the needle end, that is cut off at a right angle to the longitudinal needle axis LA2 of the injection syringe, and thus an exactly predetermined injection point is guaranteed.

In the syringe reservoir MM3, a syringe plunger MM4 is mounted to be displaceable longitudinally, whose free end is designed in a usual manner to draw in a sample manually. At the upper end of the syringe reservoir a compression spring MM5 is embedded therein, whose upper end is supported against the upper front wall of the syringe reservoir, and whose lower end acts upon the end of the syringe plunger MM4. After filling the syringe, the syringe plunger is locked along with the tensioned spring MM5 by means of a locking lever MM6. After releasing the locking MM6, the syringe plunger MM4 is pressed downward by the force of the compression spring MM5, and the sample contained in the syringe reservoir MM3 is injected into the furnace in a predetermined interval of time or at a predetermined output velocity.

This output of the predetermined sample amount at an exactly predetermined velocity or in an exactly predetermined interval of time is just as important for reproducible analysis results as the precise injection position and direction, which are ensured by the special design of the injection needle and the injection port. In a realization that is not shown, an adjustable stop or even another kind of device for adjusting the position of the end of the injection needle in the furnace may be provided, which may also play a role in the context of an optimized temperature control.

The provision of a position detector $D_{INJ}$ at the locking lever MM6 of the injection syringe MM also lies within this context, which position detector detects the position of the locking lever and thus the occurred release of the compression spring MM5, and thus in turn the initiated injection process. The detector $D_{INJ}$ sends an injection signal $S_{INJ}$ to the heating control and regulation device 12A (FIG. 2), which may process this signal for providing a drive signal (time and current intensity) for the heating modules of the furnace. The time-controlled or regulated heating of the furnace thus takes into account the injection processes which might lead to "temperature surges" in the furnace for the purpose of smoothing the temporal temperature profile and preventing temperature peaks above the desired maximum values at the furnace foot.

An alternative embodiment of the sample loading into the reaction module (combustion furnace) schematically illustrated in FIG. 4 works in a similar way. In this embodiment, a small supply tube T, which is permanently installed on the injection port P', is used in conjunction with a shut-off or three-way valve in place of a displaceable injection syringe. Here, the valve position and thus an occurring injection process may be detected by means of a similar position detector $D'_{INJ}$ as in FIG. 3, or a flow detector is provided on the small supply tube T, which detector likewise detects an injection process and delivers a corresponding injection input signal to the heating control and regulation device of the measurement arrangement.

Incidentally, FIG. 4 shows in a schematic manner that the measurement arrangement may comprise a supply control device for controlling the sample injection, which, according to the designation of the controller 12 in FIG. 1, is designated 12B. This supply control device can be supplied with temperature signals of single ones or all of the temperature sensors 11m to 11p (FIG. 2) in order to control injection processes as a function of the temperature signals, that is to say the current temperature status of the combustion furnace 11, by actuating the valve V in a differentiated manner.

The realization of the invention is not restricted to the example explained above and the herein emphasized aspects but is likewise possible in a number of modifications which are within the scope of skilled action.

The invention claimed is:

1. A measurement arrangement for determining a constituent substance and/or quality parameter of water or waste water; comprising:
   a reaction module having an internal resistance heating or infrared heating apparatus, and a head section into which a sample of the water or waste water is introduced;
   a reaction zone where thermal decomposition is performed;
   a foot section from which a reaction product is output in a carrier gas flow;
   apparatus supplying a sample of the water or waste water and a carrier gas to the reaction module; and
   a detector in the carrier gas flow;
   wherein during operation of the measurement arrangement an outer head temperature of $T_H \leq 80°$ C., and an outer foot temperature of $T_F \leq 150°$ C. at a maximum temperature in the reaction zone of $T_{MAX} \geq 1150°$ C. is maintained.

2. The measurement arrangement according to claim 1, configured for determining nitrogen and/or phosphorus and/or content of organic carbon, TOC, or chemical oxygen demand, COD.

3. The measurement arrangement according to claim 1, wherein during the operation of the measurement arrangement, an outer head temperature of $T_H \leq 70°$ C. and an outer foot temperature of $T_F \leq 150°$ C. at a maximum temperature in the reaction zone of $T_{max} \geq 1200°$ C. is maintained.

4. The measurement arrangement according to claim 1, wherein the reaction module has a two-layer or multi-layer thermal insulation comprising a macroporous layer and a microporous layer.

5. The measurement arrangement according to claim 4, wherein one of the layers of the thermal insulation is formed by prefabricated annular resistance heating/ceramic fiber modules.

6. The measurement arrangement according to claim 1, wherein the reaction module is mainly filled with a vertically layered filling of porous ceramic balls, wherein a mean ball diameter in several layers is different.

7. The measurement arrangement according to claim 1, wherein the reaction module has an inner wall of aluminum oxide or stainless steel extending at least along a length of the reaction zone, and/or in the head and foot sections in each case a reinforced sealing element having an O-ring with a Teflon sheathing is provided.

8. A measurement method for determining a constituent substance and/or quality parameter of water or waste water, comprising:
   thermally decomposing a sample of the water or waste water having a defined quantity in a reaction module that is an elongated vessel of vertical orientation having an internal resistance heating or infrared heating mechanism, a head section into which the sample is introduced, a reaction zone where the thermal decomposition is performed, and a foot section, from which a reaction product is output in a carrier gas flow;
   delivering the reaction product of the thermal decomposition to a detector in a carrier gas flow; and
   evaluating a detector signal, deriving a value of the constituent substance and/or quality parameter;
   wherein during operation of the reaction module, a head temperature of $T_H \leq 80°$ C. and a foot temperature of $T_F \leq 150°$ C. at a maximum temperature in the reaction zone of $T_{max} \geq 1150°$ C. are maintained.

9. The measurement method according to claim 8, designed for determining nitrogen and/or phosphorus and/or content of organic carbon, TOC, or chemical oxygen demand, COB.

10. The measurement method according to claim 8, wherein during the operation of the reaction module, a head temperature of $T_H \leq 70°$ C. and a foot temperature of $T_F \leq 150°$ C. at a maximum temperature in the reaction zone of $T_{max} \geq 1200°$ C. are maintained.

11. The measurement method according to claim 8, wherein during input of a sample into the reaction module, an injection input signal is generated for a heating control device of the resistance heating or infrared heating, and the heating control device is operated such as to vary power of the resistance heating or infrared heating based on the injection input signal.

12. The measurement method according to claim 11, wherein at least one temperature sensor is assigned to heating elements of the resistance heating or infrared heating, and signals of the at least one temperature sensor are supplied to corresponding control inputs of the heating control device, and the heating control device is operated such as to apply a heating current to the heating elements as a function of an output signal of the associated at least one temperature sensor and in accordance with a predetermined temperature profile of the reaction module.

13. The measurement method according to claim 11, wherein a control algorithm in the heating control device is operated such as to utilize at least an output signal of a temperature sensor, and, optionally, the injection input signal for temperature regulation in the reaction module.

14. The measurement method according to claim 8, wherein means for sample supply and carrier gas supply into the reaction module have a supply control device for automatically controlled sample supply and carrier gas supply and are operated such that temperature fluctuations within the reaction zone are minimized.

* * * * *